United States Patent
Honeycutt et al.

[11] Patent Number: 5,891,812
[45] Date of Patent: Apr. 6, 1999

[54] LIQUID ABSORBABLE NON-PERMEABLE FABRICS AND METHODS OF MAKING, USING, AND DISPOSING THEREOF

[75] Inventors: Travis W. Honeycutt, Gainesville; Baosheng Lee, Duluth; Dong Dai; Bryan Khamvongsa, both of Lawrenceville, all of Ga.; Robert E. Jones, Arden, N.C.

[73] Assignee: Isolyser Company, Inc., Norcross, Ga.

[21] Appl. No.: 869,470

[22] Filed: Jun. 5, 1997

Related U.S. Application Data

[63] Continuation of PCT/US96/16249 Oct. 11, 1996.
[51] Int. Cl.⁶ ..................................................... B32B 27/04
[52] U.S. Cl. ........................ 442/118; 128/849; 442/239
[58] Field of Search ................................ 442/50, 82, 84, 442/239, 112; 128/849

[56] References Cited

U.S. PATENT DOCUMENTS

| | | |
|---|---|---|
| 2,340,866 | 2/1944 | Dangelmajer . |
| 2,395,616 | 2/1946 | Dangelmajer . |

(List continued on next page.)

FOREIGN PATENT DOCUMENTS

| | | |
|---|---|---|
| 8902229 | 2/1990 | Brazil . |
| 010171 | 4/1980 | European Pat. Off. . |
| 0050288 | 4/1982 | European Pat. Off. . |
| 0107576 | 5/1984 | European Pat. Off. . |
| 0155150 A2 | 9/1985 | European Pat. Off. . |
| 0176316 | 4/1986 | European Pat. Off. . |
| 0272816 | 6/1988 | European Pat. Off. . |
| 0320895 | 6/1989 | European Pat. Off. . |
| 0507760 A1 | 10/1992 | European Pat. Off. . |
| 15 19 530 | 4/1970 | Germany . |
| 30 17 246 | 11/1981 | Germany . |
| 47-41741 | 10/1972 | Japan . |
| 55-71532 | 5/1980 | Japan . |
| 59-100704 | 6/1984 | Japan . |
| 60-44897 | 3/1985 | Japan . |
| 61-159995 | 7/1986 | Japan . |
| 63-200764 | 8/1988 | Japan . |
| 2-68396 | 3/1990 | Japan . |
| 5-140350 | 6/1993 | Japan . |
| 5-321105 | 12/1993 | Japan . |
| 6-248546 | 9/1994 | Japan . |
| 386161 | 1/1933 | United Kingdom . |
| 743165 | 1/1956 | United Kingdom . |
| 1187690 | 4/1970 | United Kingdom . |
| 1271424 | 4/1972 | United Kingdom . |
| 1312370 | 4/1973 | United Kingdom . |
| 1374199 | 11/1974 | United Kingdom . |
| 1451619 | 10/1976 | United Kingdom . |
| 2083762 | 3/1982 | United Kingdom . |
| 2102461 | 2/1983 | United Kingdom . |
| 2119709 | 11/1983 | United Kingdom . |
| 2211088 | 6/1989 | United Kingdom . |
| 2211196 | 6/1989 | United Kingdom . |

(List continued on next page.)

OTHER PUBLICATIONS

Encyclopedia of Polymer Science, vol. 17, 167–187 (1989).

Primary Examiner—James J. Bell
Attorney, Agent, or Firm—Needle & Rosenberg, P.C.

[57] ABSTRACT

An article made from a fabric layer permeable to a first liquid such as water, blood or urine. The article has one side that repels the liquid and another side which absorbs the liquid. The article can be disposed of by heating in a selected liquid, which dissolves or disperses the article. The article may also have a plastic layer affixed thereto to provide additional impermeability. Two of the fabric layers may be affixed with the impermeable sides facing each other to provide an article capable of absorbing fluids from both sides, yet preventing fluids from penetrating from one side to the other. An optional plastic layer may be juxtaposed between the facing sides to provide a further fluid barrier. A method of disposing of such articles comprising contacting the articles with a sufficiently hot second liquid for a sufficient period of time to disperse or dissolve substantially the articles.

84 Claims, 1 Drawing Sheet

U.S. PATENT DOCUMENTS

| | | |
|---|---|---|
| 2,408,377 | 10/1946 | Dangelmajer . |
| 2,430,949 | 11/1947 | Porter et al. . |
| 2,909,502 | 10/1959 | Matsumoto et al. . |
| 3,089,493 | 5/1963 | Galindo . |
| 3,279,511 | 10/1966 | Griffin, Jr. . |
| 3,314,809 | 4/1967 | Klug . |
| 3,372,311 | 3/1968 | Lobur . |
| 3,413,229 | 11/1968 | Bianco et al. . |
| 3,484,874 | 12/1969 | Bickenheuser . |
| 3,578,619 | 5/1971 | Reeder . |
| 3,607,812 | 9/1971 | Takigawa et al. . |
| 3,637,657 | 1/1972 | Morii et al. . |
| 3,762,454 | 10/1973 | Wilkins, Jr. . |
| 3,790,067 | 2/1974 | Scheier . |
| 3,809,077 | 5/1974 | Hansen . |
| 3,859,125 | 1/1975 | Miller et al. . |
| 3,865,918 | 2/1975 | Mitchell et al. . |
| 3,886,112 | 5/1975 | Watson et al. . |
| 3,886,610 | 6/1975 | Shelden . |
| 3,930,086 | 12/1975 | Harmon . |
| 3,931,088 | 1/1976 | Sakurada et al. . |
| 4,073,733 | 2/1978 | Yamauchi et al. . |
| 4,079,036 | 3/1978 | Ohmori et al. . |
| 4,258,849 | 3/1981 | Miller . |
| 4,279,752 | 7/1981 | Sueoka et al. . |
| 4,295,850 | 10/1981 | Haberli et al. . |
| 4,308,303 | 12/1981 | Mastroianni et al. . |
| 4,309,494 | 1/1982 | Stockel . |
| 4,343,133 | 8/1982 | Daniels et al. . |
| 4,478,971 | 10/1984 | Ballard . |
| 4,514,537 | 4/1985 | Cavanaugh . |
| 4,536,532 | 8/1985 | Miller et al. . |
| 4,568,341 | 2/1986 | Mitchell et al. . |
| 4,619,793 | 10/1986 | Lee . |
| 4,620,999 | 11/1986 | Holmes . |
| 4,651,725 | 3/1987 | Kifune et al. . |
| 4,705,712 | 11/1987 | Cashaw et al. . |
| 4,863,779 | 9/1989 | Danponte . |
| 4,868,024 | 9/1989 | Cross et al. . |
| 4,930,942 | 6/1990 | Keyes et al. . |
| 4,952,550 | 8/1990 | Wallach et al. . |
| 4,959,341 | 9/1990 | Wallach . |
| 4,959,464 | 9/1990 | Yeh . |
| 4,971,861 | 11/1990 | Watanabe et al. . |
| 5,051,222 | 9/1991 | Marten et al. . |
| 5,106,890 | 4/1992 | Maruhashi et al. . |
| 5,181,966 | 1/1993 | Honeycutt et al. . |
| 5,181,967 | 1/1993 | Honeycutt . |
| 5,183,571 | 2/1993 | Hanel et al. . |
| 5,207,837 | 5/1993 | Honeycutt . |
| 5,208,104 | 5/1993 | Ueda et al. . |
| 5,225,120 | 7/1993 | Graiver et al. . |
| 5,252,340 | 10/1993 | Honeycutt . |
| 5,268,222 | 12/1993 | Honeycutt . |
| 5,346,482 | 9/1994 | Metz . |
| 5,441,056 | 8/1995 | Weber et al. . |
| 5,538,012 | 7/1996 | Wiedner et al. . |
| 5,620,786 | 4/1997 | Honeycutt et al. . |

FOREIGN PATENT DOCUMENTS

| | | |
|---|---|---|
| 2227245 | 7/1990 | United Kingdom . |
| 2248842 | 4/1992 | United Kingdom . |
| 2254626 | 10/1992 | United Kingdom . |
| 2267711 | 12/1993 | United Kingdom . |
| WO 80/01374 | 7/1980 | WIPO . |
| WO 91/14413 | 10/1991 | WIPO . |
| WO 91/17210 | 11/1991 | WIPO . |
| WO 93/22125 | 11/1993 | WIPO . |
| WO 94/25189 | 11/1994 | WIPO . |

LIQUID ABSORBABLE NON-PERMEABLE FABRICS AND METHODS OF MAKING, USING, AND DISPOSING THEREOF

This application is a continuation of PCT/US96/16249, filed Oct. 11, 1996.

BACKGROUND OF THE INVENTION

I. Field of the Invention

The present invention relates to the field of fabrics and, particularly, to articles which are absorbent to liquids, yet not completely permeable to liquids.

II. Background of Invention

Hospital patient care generates considerable quantities of infectious medical waste in primary and acute care facilities. Such facilities have a need to provide various textile products to be used by physicians and other professionals, as well as for bedding, draperies, towels, and similar items.

At one time, virtually all textiles used in such environments were reusable. Reusable textiles were primarily made from woven fabrics of yarns and the yarns were composed of cotton or other natural fibers. However, synthetics were later developed which included fibers such as nylon and polyester. These synthetics were primarily spun from staple fibers and very little texturized synthetic filaments were in use at that time.

Approximately thirty years ago, disposable garments, covers, linens and drapes were introduced to the medical environment. When compared to the reusable garments, the disposables offered many cost- and time-saving features. For instance, hospitals were able to reduce or entirely eliminate their laundry facilities and the hospital had, for the first time, garments that exhibited significant barrier protection. Barrier protection is important in hospitals to prevent unwanted contact of the wearer to harmful liquids, infections agents, and other bodily fluids.

Another significant drawback to reusable textiles was that they could not provide liquid barrier capabilities, especially after only a few laundry cycles. However, the average lifetime of a hospital reusable was approximately 18 laundry cycles.

Current disposables are generally non-woven in composition. For instance, carded stock is often chemically bonded into fabrics. Such carded webs are treated with adhesives or bonding agents and are then calendared to form "paper-light" materials. Carded webs have recently been replaced by thermobond materials, which have a softer "hand," but which have reduced cross-directional strength.

Further current disposables are produced from air-entangled and hydroentangled fibers which produce suitable fabrics. Such non-wovens are composed mostly of polypropylene fibers or from a polyester staple with cellulose wood pulp. These hydroentangled webs display the most textile-like hand, as well as a high degree of dimensional or cross-directional strength. Non-wovens of this class, such as SONTARA® by Du Pont, are widely accepted for use in medical gowns and drapes.

Recently, the medical industry has begun reverting to the use of reusable items. This trend arose because the disposable items produced significant infectious waste products. Originally, disposables were favored because they promoted anti-septic patient contact and decreased the potential for cross-infections between patients, a significant problem with cleanable, reusable textiles. However, various federal and state regulations have subsequently reclassified much of the disposable product as "infectious," thereby making desirable the minimization of their use.

An average hospital patient produces 55 lbs. of medical waste per day. Approximately 20% of that waste is classified as "infectious." The American Hospital Association and the Centers for Disease Control recommend immediate disposal of medical waste. Medical waste is considered an occupational hazard for health care workers, but is not considered an environmental safety problem. The most preferable way to contain infectious medical waste is to disinfect it at the point of generation and dispose of the treated medical waste with minimum handling and storage on premises.

As a result, consumption of medical disposable woven or non-woven products has been growing at a rate of approximately 10% a year. In 1988, sales totaled approximately 1.155 billion dollars. It is projected that as of the end of 1996, sales of medical disposable non-woven products will have exceeded two and a half billion dollars. In the United States, there are at least 30 million surgical procedures performed each year. After each surgical procedure, it is necessary that the operating theater be disinfected before a new procedure is performed to minimize any exposure the patients may bring to other patients or staff. This is particularly important in light of today's increasingly stringent regulations regarding occupational exposure to blood and bodily fluids.

One of the most prevalent items in the surgical theater as well as in the clinical environment is the use of surgical drapes and surgical gowns. These textiles are highly likely to come into contact with infectious materials in the form of spills, splashes, drips or general runoff of potentially hazardous fluids such as blood, bodily liquids and irrigation products presently involved in virtually all operating procedures. Cleaning of soiled gowns and drapes also leads to considerable opportunity for additional hazardous exposure to people that are employed to clean the garments after they are used. Furthermore, conventional gowns and drapes, if disposed of either through landfill or incineration, provide ample opportunity for reinfection.

In addition, traditional medical textiles such as gowns and drapes are constructed of a fluid absorbent fabric. While this fabric permits containment of spilled or splashed liquids, the liquids are quite capable of permeating the textile and thereby recontracting the patient or the medical worker.

The invention herein solves the drawbacks of the prior art by providing a textile suitable for use in the medical environment, such as for use as a gown or a drape, which is capable of absorbing harmful liquids yet preventing contact of the liquids with a patient or worker. Moreover, the invention, in another embodiment, provides such a textile which can be disposed of without additional risk of contamination or reinfection. In addition, the invention provides a textile disposal process that does not require the article to be introduced to a landfill, where it would be environmentally detrimental as well as potentially infectious. The invention also provides an alternative textile in which these desirable capabilities are provided for in a unitary, i.e., one piece, non-laminated article.

SUMMARY OF THE INVENTION

The present invention provides an article comprising a fabric layer permeable to a first liquid and having a first side and an opposed second side, wherein the first side of the fabric layer further comprises a coating repellent to the first liquid, wherein the coating substantially penetrates into the first side of the fabric layer, thereby forming a first liquid proof first side. In a further embodiment, the fabric layer is soluble in a second liquid when the second liquid is hot and insoluble in the second liquid when the second liquid is cold. In a further embodiment, the article is a surgical fabric. In yet a further embodiment, the article is a surgical drape. In a further embodiment, the fabric layer dissolves in the second liquid only at a temperature above 37° C.

In an alternative embodiment, the article further comprises a plastic layer having a first side and an opposed second side, wherein the first side of the plastic layer faces the first side of the fabric layer.

In yet another embodiment, the present invention provides an article comprising a first fabric layer permeable to a first liquid and having a first side and an opposed second side, wherein the first side of the first fabric layer further comprises a coating repellent to the first liquid, wherein the coating substantially penetrates into the first side of the first fabric layer, thereby forming a first liquid proof first side of the first fabric layer, and a second fabric layer permeable to the first liquid and having a first side and an opposed second side, wherein the first side of the second fabric layer further comprises a coating repellent to the first liquid, wherein the coating substantially penetrates into the first side of the second fabric layer, thereby forming a first liquid proof first side of the second fabric layer, whereby the first liquid proof first side of the first fabric layer faces the first liquid proof first side of the second fabric layer. In another embodiment, the first and second fabric layers are soluble in a second liquid when the second liquid is hot and insoluble in the second liquid when the second liquid is cold. In a further embodiment, the article is a surgical fabric. In yet a further embodiment, the article is a surgical drape. In a further embodiment, the fabric layer dissolves in the second liquid only at a temperature above 37° C.

In a further embodiment, at least one plastic layer is disposed between the first liquid proof side of the first fabric layer and the first liquid proof side of the second fabric layer. In a further embodiment, the first and second fabric layers are soluble in a second liquid when the second liquid is hot and insoluble in the second liquid when the second liquid is cold.

In yet another embodiment, the present invention provides a method of disposing of the articles of the invention, wherein the fabric layer is soluble in a second liquid when the second liquid is hot and insoluble in the second liquid when the second liquid is cold, comprising contacting the article with a sufficiently hot second liquid for a sufficient period of time to disperse or dissolve substantially the article.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE PREFERRED EMBODIMENTS

Figure 1:
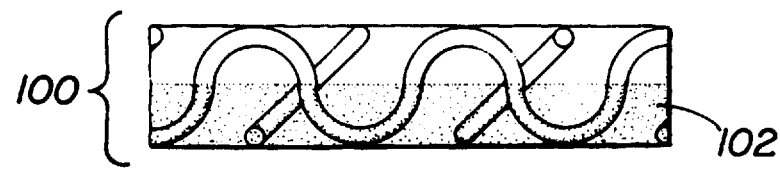
FIG. 1 shows one embodiment of an article 100 of the present invention having a waterproof layer 102 on one side.

The present invention may be understood more readily by reference to the following detailed description of preferred embodiments of the invention and the Figures.

Before the present methods and apparatuses are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

Throughout this application, where publications are referenced, the disclosures of these publications in their entireties are hereby incorporated by reference into this application in order to more fully describe the state of the art to which this invention pertains.

As used herein, the term "fabric layer" refers to a woven or non-woven fabric material suitable for producing textile-like articles. One or more layers of the fabric may comprise a "fabric layer".

As used herein, the term "permeable" refers to the ability of a particular article or item to permit fluids, such as liquids, to pass therethrough or to penetrate therein.

As used herein, the term "liquid" refers to fluids such as water, blood, and urine.

As used herein, the term "coating" refers to a distinct portion of a surface having the stated properties. The "coating" may be contiguous with the substrate or may comprise a separate layer affixed thereto.

As used herein, the term "repellent", when used in connection with a coating, describes the ability of the coating to resist, at least partially, permeation or penetration by the specified fluid. Hence, a "water repellent" article resists water from permeating the article.

As used herein, the term "substantially penetrates" refers to the extent to which the stated material has integrated into the specified substrate. Substantial penetration, as used herein, involves a penetration into the item of from about 10 to about 90%, more preferably 20 to 80%, most preferably about 50% of the thickness of the item.

As used herein, the term "dispersable" refers to an item which may or may not dissolve completely in the stated fluid, such as a liquid, but does structurally fragment or break apart in the presence of the fluid.

As used herein, the term "hot" is used to refer to temperatures above about body temperature, or 37° C. More preferably, "hot" refers to temperatures above 40° C., more preferably to temperatures above 45° C., even more preferably to temperatures above 50° C., even more preferably to temperatures above 75° C., and most preferably to temperatures above 90° C. Similarly, "cold" is used to refer to temperatures below about body temperature, or 37° C. More preferably, "cold" refers to temperatures below 30° C., more preferably to temperatures below 25° C., and even more preferably to temperatures below 20° C.

As used herein, the term "surgical fabric" refers to a textile like woven or nonwoven article suitable for use in an operating room. Such fabrics include, but are not limited to gowns, drapes, and masks. Thus, a "surgical drape" is one type of "surgical fabric."

As used herein, especially with respect to drapes, the term "operating aperture" refers to an opening cut through one of the articles of the invention so as to permit a surgical or other procedure to be performed through the opening.

As used herein with respect to various layers of the article, the terms "face", "facing" and "faces" refer to two or more layers that are positioned adjacent to one another with the indicated sides directed toward one another. Facing layers need not be in contact and may, optionally, have further matter disposed therebetween.

As used herein, the term "laminated" refers to the process of producing an article by accumulating layers of specified materials.

As used herein, the term "adhered" refers to temporary or permanent affixation of the specified items. Adherence may occur with or without additional materials such as adhesives. Suitable adhesives, where used, include glues and the like.

The present invention therefore provides, in one embodiment, an article comprising a fabric layer permeable to a first liquid and having a first side and an opposed second side, wherein the first side of the fabric layer further comprises a coating repellent to the first liquid, wherein the coating substantially penetrates into the first side of the fabric layer, thereby forming a first liquid proof first side.

In an alternative embodiment, the fluid impermeability of the article is further ensured by providing a plastic layer having a first side and an opposed second side. The plastic layer is oriented with respect to the fabric layer such that the first side of the plastic layer faces the first side of the fabric layer. In one embodiment, the plastic layer comprises any polymer having a melting temperature below 100° C. Suitable polymers include, but are not limited to, polycaprolactone or poly(vinyl) alcohol. Moreover, the polymer is preferably biodegradable, but non-biodegradable polymers are also suitable. Such non-biodegradable polymers include, but are not limited to, polyethylene and polyolefin copolymer, polyethylene and polymethylacrylate copolymer, and polyethylene polyesters.

In still a further embodiment, the fabric layer and the plastic layer are laminated. Alternatively, the fabric layer and the plastic layer may adhered together with an adhesive. One of ordinary skill in the art would recognize that there are numerous suitable adhesives that could be used, such as, but not limited to, a glue.

In yet another embodiment, the present invention provides an article comprising a first fabric layer permeable to a first liquid and having a first side and an opposed second side. The first side of the first fabric layer is further coated with a coating repellent to the first liquid. Preferably, the coating substantially penetrates into the first side of the first fabric layer. The coated, penetrated first fabric layer thereby forms a first liquid proof first side of the first fabric layer. In addition, the article also comprises a second fabric layer permeable to the first liquid and having a first side and an opposed second side. The first side of the second fabric layer also has a coating repellent to the first liquid placed thereon. This coating also substantially penetrates into the first side of the second fabric layer and forms a first liquid proof first side of the second fabric layer. The article is formed such that the first liquid proof first side of the first fabric layer faces the first liquid proof first side of the second fabric layer. In the fashion a particularly preferable article is formed such that the article can absorb contaminants emanating from the environment and from the patient or wearer, yet the article is capable of preventing the contaminants from passing through the article and becoming a further hazard.

In a preferred embodiment, the first and second fabric layers are soluble in a second liquid when the second liquid is hot and insoluble in the second liquid when the second liquid is cold. In a preferred embodiment, the first liquid is water. In another preferred embodiment, the second liquid is water. In one embodiment, the article is a surgical fabric, such as a surgical drape. In another embodiment, the fabric layer of the drape has a portion cut therefrom, thereby defining an operating aperture of the drape.

In yet another embodiment, the article also has at least one plastic layer disposed between the first liquid proof side of the first fabric layer and the first liquid proof side of the second fabric layer. Thus, the plastic layer may be comprised of a single layer of plastic, or, alternatively, may be comprised of two or more plastic layers adjacent to one another. For instance, the article could be made from two of the articles of FIG. 1, joined at their plastic layer sides. The "total thickness" of the at least one plastic layer refers to the cumulative thickness of all of the plastic layers. The plastic layer is preferably of from 1 to 2 mils in thickness. This article provides an enhanced fluid barrier between the first and second sides of the article. In a preferred embodiment, the at least one plastic layer is adhered to both the first liquid proof side of the first fabric layer and the first liquid proof side of the second fabric layer. In preferred embodiments, each fabric layers has a thickness of from 0.02 to 60 mils, preferably about 11 mils. More than one fabric layer may be used.

In a further embodiment of the articles of the invention, the fabric layer is soluble in a second liquid when the second liquid is hot and insoluble in the second liquid when the second liquid is cold. In one embodiment, the first liquid is water, saline, blood, urine, surgical irrigation fluid runoff, alcohol solutions, other bodily fluids, or the like.

The coating repellent to the liquid is a portion of the fabric that has been treated with a liquid repellent. Where the liquid to be repelled is water or, at least, aqueous, the water repellent can be any typical water repellent known in the art. However, in the application as a reenforcement drape, the water repellent is applied to the fabric on the underside of the fabric, i.e. the side that is placed in contact with the body of the patient. That is, the waterproof layer faces toward the patient's body. In addition to being a water repellent article, in one embodiment, the article is also absorbent and repellent to alcohol. As described herein, the water repellent is applied to only one side, thereby creating a fabric having an absorbent side and a water repellent side opposite the absorbent side. Complete penetration of the repellent into the fabric layer would preclude the article from having a fluid absorbent side. Therefore, the repellent should substantially, but not completely, penetrate the fabric layer. Penetration is preferably from 10 to 90% of the thickness of the layer, more preferably from 20 to 80%, even more preferably 40 to 60% of the thickness, and most preferably about 50% of the thickness of the layer.

Disposal of the articles of the invention is accomplished by dissolution at the proper temperature in the second liquid. In a preferred embodiment, the second liquid is water. However, other solvents may be used and materials may be chosen so that the articles are disposable as described herein.

As noted above, because of the desirability of disposing of the articles, preferred articles include surgical fabrics and surgical drapes. For surgical drapes, the fabric layer of the drape can, optionally, have a portion cut therefrom. This opening defines an operating aperture on the drape.

In further embodiments of the articles, the fabric layer has a density of from 20 to about 120 g/m$^2$, more preferably of from 40 to about 100 g/m², even more preferably from about 60 to about 80 g/m², and most preferably about 70 g/m². In yet another embodiment, the fabric layer has a thickness of from about 0.02 mils to about 60 mils.

In yet other embodiments, the fabric layer dissolves in the second liquid only at a temperature above 37° C., more preferably only at a temperature above 40° C., still more preferably only at a temperature above 45° C., even more preferably only at a temperature above 50° C., even more preferably only at a temperature above 75° C., and most preferably only at a temperature above 90° C.

In one embodiment, the fabric comprises poly(vinyl) alcohol. In a preferred embodiment, the poly(vinyl) alcohol is a greater than 95% saponified poly vinyl acetate, more preferably greater than 98% saponified poly vinyl acetate, even more preferably greater than 99% saponified poly vinyl acetate, and even more preferably is greater than 99.99% saponified poly vinyl acetate. The fabric layer is an absorbent material so that the liquid can be absorbed quickly without spillage onto the patient's body. Suitable hot liquid soluble, cold liquid insoluble materials, such as poly vinyl alcohol materials, are described in detail in U.S. Pat. Nos. 5,181,966, 5,181,967, and 5,207,837, the contents of which are hereby incorporated by this reference. Other suitable materials for forming the fabric have been listed above with respect to the plastic layer.

In addition to these articles, the present invention also provides a disposal method applicable to the articles. In particular, the present invention provides a method of disposing of the articles of the invention, especially where the fabric layer is soluble in a second liquid when the second liquid is hot and insoluble in the second liquid when the second liquid is cold. The method involves contacting the article with a sufficiently hot second liquid for a sufficient period of time to disperse or dissolve substantially the article. Thus, if the second liquid is water and the sufficient heat is 90° C., then boiling the article in water (at 100° C.) would thereby disperse or dissolve substantially the article. In one embodiment, the method is used to dispose of a surgical fabric such as a surgical drape. In a preferred embodiment, the articles to be disposed are introduced into a washing machine and are agitated in hot water for a period of time sufficient to effect disposal. Preferably, the hot water is of a temperature of at least 50° C., more preferably at least 90° C., and even more preferably at least 95° C. In addition, the period of time in the machine is from about 2 minutes to about 40 minutes, and more preferably is from about 10 to about 30 minutes. Depending upon the composition of the article, the runoff from the machine may be released to the sewage system (if all biodegradable) or the insoluble or non-biodegradable components may be reclaimed via filtration or dehydration or other known separating processes.

Moreover, the present invention provides the above-described articles, wherein the coating penetrates into the first side of the fabric layer from 10% to 90% of the thickness of the fabric layer.

In a further embodiment of the present invention, the coating comprises a fluorocarbon and a wax. Suitable waxes and fluorocarbons include, but are not limited to, paraffin waxes and perfluorinated polyacrylate copolymers. One method of finishing the article is to contact the article with a finishing composition having the following ingredients:

| Ingredient | Percent (by weight) |
|---|---|
| 1. Pigments | 0.01 to 1.0 [(optional) Such as phthalocyanine pigment (blue) (Sandoz) and 3,3'-dichlorobenzidine derivatives (yellow) (Sandoz)] |
| 2. Wax emulsion | 2 to 50 [10% paraffin wax, 10% melamine resin, 80% water] |
| 3. Fluorochemical | 2–50 [perfluorinated polyacrylate copolymer] |
| 4. Binder | 0.01 to 30.0 [(optional, use if pigments were employed) polyvinyl alcohol solution of hot water soluble binders] |
| 5. Foaming agent | 0.01 to 30.0 [surfactant, preferably of a class that is decomposed by heating during curing] |
| 6. Water | Remainder to 100 |

This composition provides for a wet pick-up of preferably 25%, but wet pick-up values from 0% to 200% may be suitable depending upon the particular application, and is applied to one side of the fabric layer, penetrating from about 10 to about 90%, more preferably 20 to about 80%, and most preferably about 50% of the thickness of the layer, as described elsewhere herein. One device suitable for the application of the finishing composition is shown in U.S. Pat. No. 4,655,056, the contents of which are hereby incorporated in their entirety by this reference.

Figure 2:
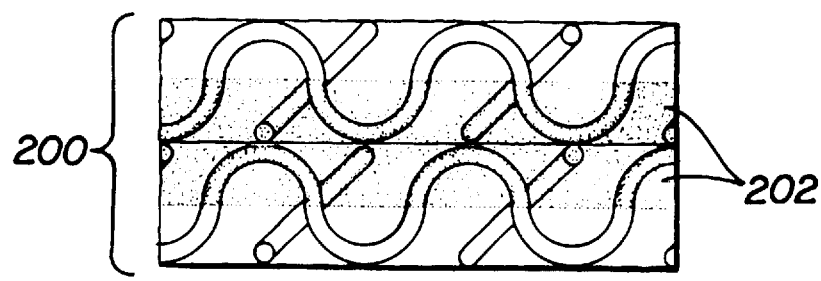
FIG. 2 shows another embodiment of an article 200 of the present invention having a waterproof layer 202.
Figure 3:
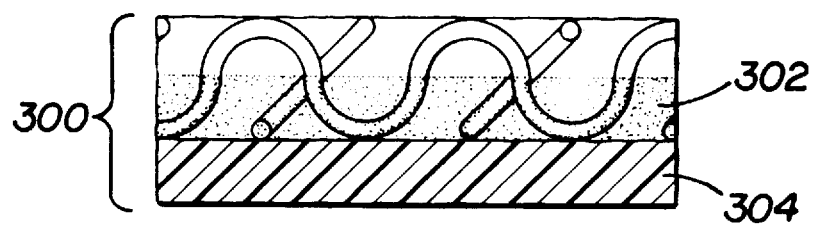
FIG. 3 shows another embodiment of an article 300 of the present invention having a water proof layer 302 and plastic film or sheet layer 304.
Figure 4:
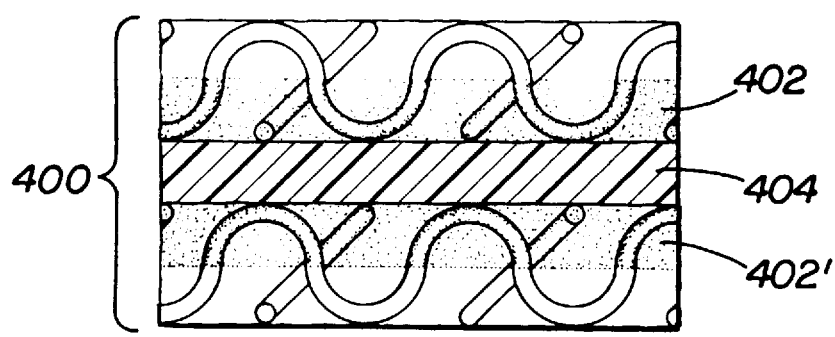
FIG. 4 shows another embodiment of an article 400 of the present invention having two water proof layers, 402 and 402', and a plastic film or sheet layer 404.

Four of the preferred embodiments are set forth in FIGS. 1–4. FIG. 1 is a fabric having a waterproof layer on one side. The waterproof layer is the side that is placed closest to the patient's body. FIG. 2 shows two articles of FIG. 1 joined together at the waterproof layer. This allows the drape to be placed on the patient on either side of the drape. The embodiment shown in FIG. 3 is the same as the embodiment shown in FIG. 1, except a plastic film or sheet layer is attached to the waterproof layer. The plastic serves as an additional waterproof layer and/or a reenforcement layer. Finally, FIG. 4 shows the same embodiment as FIG. 2, except that a plastic layer is inserted between the two waterproof layers.

Without any intention to limit the scope of this invention in any way, the article shown in FIG. 1 is preferably, but not exclusively, intended for minor surgery. The article absorbs fluids contacting the top surfaces, yet keeps the bottom of the fabric dry. The article shown in FIG. 2 is also intended for minor surgery. The article absorbs fluids from the top, the treated middle layer keeps fluids from penetrating all the way through the article. The article also absorbs fluid from the bottom. The article shown in FIG. 3 is intended for major surgery. The additional plastic layer further provides a fluid barrier. Finally, the article shown in FIG. 4 is also intended for major surgery. As with the article shown in FIG. 2, this article provides for absorption of fluids from both sides of the surgical fabric.

Generally, the articles of the present invention are made as follows. A chosen amount of the polymer fibers are formed into a fabric layer of about 0.02 to 30 mil thickness or having a density of about 10–100 g/m². The above-specified finishing composition is applied to the fabric layer, on one side only, using through foaming application or by printing application. In this fashion, the finishing composition does not penetrate through to the opposite side of the fabric, but instead only partially penetrates the layer. Preferably, the finishing composition penetrates from 10 to 90% of the thickness of the fabric layer, more preferably from 20 to 80% of the thickness, and most preferably about 50% of the thickness of the layer. This article is shown in FIG. 1.

The article shown in FIG. 2 is, generally, made as follows. Two of the articles of FIG. 1 may affixed, either by lamination or by using an adhesive, together at their repellent sides to form the article of FIG. 2.

The article shown in FIG. 3 is, generally, made as follows. The above-described article (FIG. 1) is further processed in that one or more plastic layers are affixed to the article using either a laminating machine or simply by using an adhesive, such as a glue.

The article shown in FIG. 4 is, generally, made by one of two processes. First, an article of FIG. 1 and an article of FIG. 3 may be affixed together either by lamination or by using an adhesive. Specifically, the repellent side of the article of FIG. 1 is affixed to the plastic layer(s) of the article of FIG. 3. Alternatively, two of the articles of FIG. 3 may affixed together at their plastic layer sides to form the article of FIG. 4. Additional plastic layers may be introduced, if desired.

The following examples are put forth so as to provide those of ordinary skill in the art with a complete disclosure and description of how the compounds articles claimed herein are made, used and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in °C. and is at room temperature, and pressure is at or near atmospheric.

A sample roll of the article shown in FIG. 1 was prepared. Cross-directional and machine-directional tensile strength was measured and was, on average, respectively, 65.9 and 45.5N/50 mm. In addition, elongation (at break) of the article was tested in the cross-directional and machine directional direction and was, on average, found to be 16.5 and 8.4%, respectively. In addition, water repellency was measured using a Mullen Burst test and occurred at 29.0 psi. Cross-directional and machine-directional Elmendorf tear measurements were found to be 851 and 1572, respectively. The weight of the representative sample was 62.2 g/m². Repellency was further evaluated using the Water Impact Penetration Test (AATCC Test 42) and was found to average 0.7. Finally, repellency was measured by a Hydrostatic Pressure test and a mean reading of 21.9 cm was measured.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. An article comprising a fabric layer permeable to a first liquid and having a first side and an opposed second side, wherein the first side of the fabric layer further comprises a coating repellent to the first liquid, wherein the coating substantially penetrates into the first side of the fabric layer thereby forming a first liquid proof first side, and wherein the fabric layer is soluble in a second liquid when the second liquid is hot and insoluble in the second liquid when the second liquid is cold.

2. The article of claim 1, wherein the first liquid is water.

3. The article of claim 1, wherein the second liquid is water.

4. The article of claim 1, wherein the article is a surgical fabric.

5. The article of claim 1, wherein the article is a surgical drape.

6. The article of claim 5, wherein the fabric layer of the drape has a portion cut therefrom, thereby defining an operating aperture of the drape.

7. The article of claim 1, wherein the fabric layer has a thickness of from 0.02 to about 60 mils.

8. The article of claim 1, wherein the fabric layer dissolves in the second liquid only at a temperature above 37° C.

9. The article of claim 1, wherein the fabric layer dissolves in the second liquid only at a temperature above 40° C.

10. The article of claim 1, wherein the fabric layer dissolves in the second liquid only at a temperature above 45° C.

11. The article of claim 1, wherein the fabric layer dissolves in the second liquid only at a temperature above 50° C.

12. The article of claim 1, wherein the fabric layer dissolves in the second liquid only at a temperature above 75° C.

13. The article of claim 1, wherein the fabric layer dissolves in the second liquid only at a temperature above 90° C.

14. The article of claim 1, wherein the fabric comprises poly(vinyl) alcohol.

15. The article of claim 14, wherein the poly(vinyl) alcohol is a greater than 95% saponified poly vinyl acetate.

16. The article of claim 1, further comprising a plastic layer having a first side and an opposed second side, wherein the first side of the plastic layer faces the first side of the fabric layer.

17. The article of claim 16, wherein the plastic layer comprises poly(vinyl) alcohol or polycaprolactone copolymer.

18. The article of claim 16, wherein the fabric layer and the plastic layer are laminated.

19. The article of claim 16, wherein the fabric layer and the plastic layer are adhered together with an adhesive.

20. The article of claim 19, wherein the adhesive is a glue.

21. The article of claim 16, wherein the fabric layer is soluble in a second liquid when the second liquid is hot and insoluble in the second liquid when the second liquid is cold.

22. The article of claim 16, wherein the first liquid is water.

23. The article of claim 21, wherein the second liquid is water.

24. The article of claim 16, wherein the article is a surgical fabric.

25. The article of claim 16, wherein the article is a surgical drape.

26. The article of claim 25, wherein the fabric layer of the drape has a portion cut therefrom, thereby defining an operating aperture of the drape.

27. The article of claim 16, wherein each fabric layer has a thickness of from about 0.02 mils to about 60 mils.

28. The article of claim 21, wherein the fabric layer dissolves in the second liquid only at a temperature above 37° C.

29. The article of claim 21, wherein the fabric layer dissolves in the second liquid only at a temperature above 40° C.

30. The article of claim 21, wherein the fabric layer dissolves in the second liquid only at a temperature above 45° C.

31. The article of claim 21, wherein the fabric layer dissolves in the second liquid only at a temperature above 50° C.

32. The article of claim 21, wherein the fabric layer dissolves in the second liquid only at a temperature above 75° C.

33. The article of claim 21, wherein the fabric layer dissolves in the second liquid only at a temperature above 90° C.

34. The article of claim 16, wherein the fabric comprises poly(vinyl) alcohol.

35. The article of claim 34, wherein the poly(vinyl) alcohol is a greater than 95% saponified poly vinyl acetate.

36. An article comprising:
   a) a first fabric layer permeable to a first liquid and having a first side and an opposed second side, wherein the first side of the first fabric layer further comprises a coating repellent to the first liquid, wherein the coating substantially penetrates into the first side of the first fabric layer, thereby forming a first liquid proof first side of the first fabric layer; and
   b) a second fabric layer permeable to the first liquid and having a first side and an opposed second side, wherein the first side of the second fabric layer further comprises a coating repellent to the first liquid, wherein the coating substantially penetrates into the first side of the second fabric layer, thereby forming a first liquid proof first side of the second fabric layer, whereby the first liquid proof first side of the first fabric layer faces the first liquid proof first side of the second fabric layer.

37. The article of claim 36, wherein the first and second fabric layers are soluble in a second liquid when the second liquid is hot and insoluble in the second liquid when the second liquid is cold.

38. The article of claim 36, wherein the first liquid is water.

39. The article of claim 37, wherein the second liquid is water.

40. The article of claim 36, wherein the article is a surgical fabric.

41. The article of claim 36, wherein the article is a surgical drape.

42. The article of claim 41, wherein the first and second fabric layers of the drape have a portion cut therefrom, thereby defining an operating aperture of the drape.

43. The article of claim 36, wherein the first and second fabric layers have, independently, a thickness of from 0.02 to 60 mils.

44. The article of claim 37, wherein the first and second fabric layers dissolve in the second liquid only at a temperature above 37° C.

45. The article of claim 37, wherein the first and second fabric layers dissolve in the second liquid only at a temperature above 40° C.

46. The article of claim 37, wherein the first and second fabric layers dissolve in the second liquid only at a temperature above 45° C.

47. The article of claim 37, wherein the first and second fabric layers dissolve in the second liquid only at a temperature above 50° C.

48. The article of claim 37, wherein the first and second fabric layers dissolve in the second liquid only at a temperature above 75° C.

49. The article of claim 37, wherein the first and second fabric layers dissolve in the second liquid only at a temperature above 90° C.

50. The article of claim 36, wherein the first and second fabric layers comprise, independently, poly(vinyl) alcohol.

51. The article of claim 50, wherein the poly(vinyl) alcohol is a greater than 95% saponified poly vinyl acetate.

52. The article of claim 36, wherein the first fabric layer is adhered to the second fabric layer.

53. The article of claim 36, further comprising at least one plastic layer disposed between the first liquid proof side of the first fabric layer and the first liquid proof side of the second fabric layer.

54. The article of claim 53, wherein the at least one plastic layer is adhered to both the first liquid proof side of the first fabric layer and the first liquid proof side of the second fabric layer.

55. The article of claim 53, wherein the first and second fabric layers are soluble in a second liquid when the second liquid is hot and insoluble in the second liquid when the second liquid is cold.

56. The article of claim 53, wherein the first liquid is water.

57. The article of claim 55, wherein the second liquid is water.

58. The article of claim 53, wherein the article is a surgical fabric.

59. The article of claim 53, wherein the article is a surgical drape.

60. The article of claim 59, wherein the first and second fabric layers of the drape have a portion cut therefrom, thereby defining an operating aperture of the drape.

61. The article of claim 53, wherein the first and second fabric layers have, independently, a thickness of from 0.02 to 60 mils and the at least one plastic layer has a thickness of from 1 to 2 mils.

62. The article of claim 55, wherein the first and second fabric layers dissolve in the second liquid only at a temperature above 37° C.

63. The article of claim 55, wherein the first and second fabric layers dissolve in the second liquid only at a temperature above 40° C.

64. The article of claim 55, wherein the first and second fabric layers dissolve in the second liquid only at a temperature above 45° C.

65. The article of claim 55, wherein the first and second fabric layers dissolve in the second liquid only at a temperature above 50° C.

66. The article of claim 55, wherein the first and second fabric layers dissolve in the second liquid only at a temperature above 75° C.

67. The article of claim 55, wherein the first and second fabric layers dissolve in the second liquid only at a temperature above 90° C.

68. The article of claim 53, wherein the first and second fabric layers comprise, independently, poly(vinyl) alcohol.

69. The article of claim 68, wherein the poly(vinyl) alcohol is a greater than 95% saponified poly vinyl acetate.

70. The article of claim 1, wherein the coating penetrates into the first side of the fabric layer from 10% to 90% of the thickness of the fabric layer.

71. The article of claim 1, wherein the coating comprises a fluorocarbon and a wax.

72. The article of claim 1, wherein the coating penetrates into the first side of the fabric layer from 10% to 90% of the thickness of the fabric layer.

73. The article of claim 1, wherein the coating comprises a fluorocarbon and a wax.

74. The article of claim 16, wherein the coating penetrates into the first side of the fabric layer from 10% to 90% of the thickness of the fabric layer.

75. The article of claim 16, wherein the coating comprises a fluorocarbon and a wax.

76. The article of claim 36, wherein the coating penetrates into the first side of the fabric layer from 10% to 90% of the thickness of the fabric layer.

77. The article of claim 36, wherein the coating comprises a fluorocarbon and a wax.

78. The article of claim 53, wherein the coating penetrates into the first side of the fabric layer from 10% to 90% of the thickness of the fabric layer.

79. The article of claim 53, wherein the coating comprises a fluorocarbon and a wax.

80. A method of disposing of the article of claim 1, comprising contacting the article with a sufficiently hot second liquid for a sufficient period of time to disperse or dissolve substantially the article.

81. The method of claim 80, wherein the article is a surgical drape.

82. A method of disposing of the article of claim 16, comprising contacting the article with a sufficiently hot second liquid for a sufficient period of time to disperse or dissolve substantially the article.

83. A method of disposing of the article of claim 36, comprising contacting the article with a sufficiently hot second liquid for a sufficient period of time to disperse or dissolve substantially the article.

84. A method of disposing of the article of claim 53, comprising contacting the article with a sufficiently hot second liquid for a sufficient period of time to disperse or dissolve substantially the article.

* * * * *